United States Patent
Wagler et al.

(10) Patent No.: US 7,314,567 B2
(45) Date of Patent: Jan. 1, 2008

(54) METHOD FOR TRANSFERRING HETEROGENEOUS LIQUIDS IN MICROCHANNELS WITHOUT THE OCCURRENCE OF MIXING

(75) Inventors: Patrick Wagler, Boppard (DE); John Simpson McCaskill, Bonn (DE); Tobias Foster, Köln (DE)

(73) Assignee: ProtoLife Srl., Marghera, Venezia (IT)

( * ) Notice: Subject to any disclaimer, the term of this patent is extended or adjusted under 35 U.S.C. 154(b) by 289 days.

(21) Appl. No.: 10/515,873

(22) PCT Filed: May 26, 2003

(86) PCT No.: PCT/EP03/05501

§ 371 (c)(1),
(2), (4) Date: Aug. 31, 2005

(87) PCT Pub. No.: WO03/099407

PCT Pub. Date: Dec. 4, 2003

(65) Prior Publication Data

US 2006/0096923 A1    May 11, 2006

(30) Foreign Application Priority Data

May 24, 2002   (DE) .............................. 102 23 137

(51) Int. Cl.
*B01D 15/08* (2006.01)

(52) U.S. Cl. ................... 210/656; 210/659; 210/198.2; 422/82; 422/100; 204/450; 137/13; 137/825; 436/180

(58) Field of Classification Search ............... 210/635, 210/656, 659, 198.2; 422/82, 100; 204/450; 137/13, 825; 436/180
See application file for complete search history.

(56) References Cited

U.S. PATENT DOCUMENTS 4,028,056 A    6/1977  Snyder et al.

(Continued)

FOREIGN PATENT DOCUMENTS

EP    0 815 940 A2    1/1998

(Continued)

OTHER PUBLICATIONS

Takasi Nisisako et al., "Droplet Formation in a Microchannel Network," The Royal Society of Chemistry, Lab Chip, vol. 2, pp. 24-26, Jan. 2002.

(Continued)

*Primary Examiner*—Ernest G. Therkorn
(74) *Attorney, Agent, or Firm*—Shumaker & Sieffert, P.A.

(57) ABSTRACT

In the method for mixing-free transport of homogeneous liquids in microchannels a heterogeneous liquid flow (14) is autonomously divided into portions, transported over a distance and then autonomously recombined. When the flow is divided into portions, individual volumes of a second liquid (16), which may be but must not be homogeneous, are introduced between volume fractions lying one behind the other of the heterogeneous liquid flow (14). While the volume fractions of the heterogeneous liquid (14) that lye close to one another would mix with each other without this measure being taken, separation of the individual volume fractions allows these volume fractions, and thus the heterogeneous liquid (14), to be transported over large distances without any mixing occurring. Treatment of the volume fractions of the heterogeneous liquid (14) requires separation of the liquid flow (12) of alternating volume fractions of the two liquids (14,16) such that again two flows are produced, one of which being the heterogeneous starting liquid and the other being the second liquid. Since both processes can take place autonomously by self-organization of the phases, an overall solution for the mixing-free transport of a heterogeneous liquid without employment of expensive fractionating apparatus can be achieved.

6 Claims, 1 Drawing Sheet

U.S. PATENT DOCUMENTS

| | | | |
|---|---|---|---|
| 4,399,102 A | 8/1983 | Karlberg et al. | |
| 6,488,894 B1 * | 12/2002 | Miethe et al. | 422/100 |
| 7,238,268 B2 * | 7/2007 | Ramsey et al. | 204/451 |
| 2002/0166592 A1 * | 11/2002 | Liu et al. | 137/825 |
| 2004/0007463 A1 * | 1/2004 | Ramsey et al. | 204/450 |
| 2004/0259268 A1 * | 12/2004 | Jacobs et al. | 436/180 |
| 2005/0121324 A1 * | 6/2005 | Park et al | 204/451 |
| 2005/0189225 A1 * | 9/2005 | Liu et al. | 204/600 |
| 2005/0217741 A1 * | 10/2005 | Bohm | 137/828 |

FOREIGN PATENT DOCUMENTS

| | | |
|---|---|---|
| WO | WO 99/25475 | 11/1998 |
| WO | WO 01/12327 | 11/2003 |

OTHER PUBLICATIONS

Todd Thorsen et al., "Dynamic Pattern Formation in a Vesicle-Generating Microfludic Device," The American Physical Society, Physical Review Letters, vol. 86, No. 18, pp. 4163-4166, Apr. 2001.

Lachlan M. Grant et al., "Effect of Substrate Hydrophobicity on Surface—Aggregate Geometry:: Zwitterionic and Nonionic Surfactants," American Chemical Society, J. Phys. Chem. B, vol. 101, pp. 5337-5345, Apr. 1997.

Michael J. Clifton, "Continous-flow Electrophoresis in the Taylor Regime: A New Possibility for Preparative Electrophoresis," Journal of Chromatography A, vol. 757, pp. 193-202, Jul. 1996.

Sir Geoffrey Taylor F.R.S., "Dispersion of Soluble Matter in Solvent Flowing Slowly Through a Tube," pp. 186-203, Mar. 1953.

K.V. Schubert et al., "Nonionic Microemulsions," Ber. Bunsenges. Phys. Chem., vol. 100, pp. 190-205, 1996.

International Search Report, PCT/EP03/05501, 5 pgs., dated Nov. 6, 2003.

Copy of International Preliminary Examination Report, PCT Application No. PCT/EP2003/005501, mailed Apr. 28, 2005, 6 pgs.

* cited by examiner

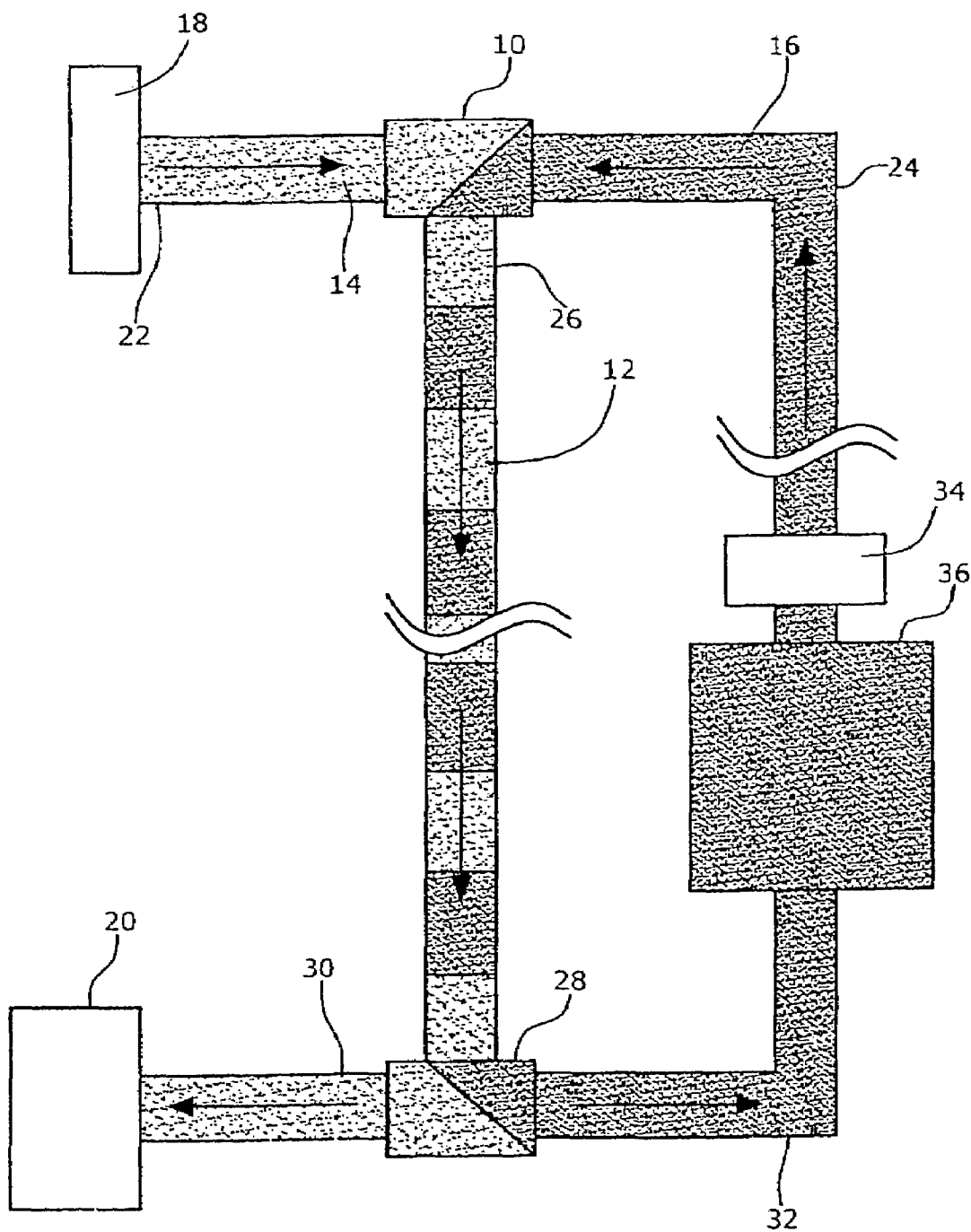

METHOD FOR TRANSFERRING HETEROGENEOUS LIQUIDS IN MICROCHANNELS WITHOUT THE OCCURRENCE OF MIXING

REFERENCE TO RELATED APPLICATIONS

This application is a 371 of PCT/EP03/03674 filed May 26, 2003.

The invention relates to a method for mixing-free transport of heterogeneous liquids in microchannels. In particular, the invention relates to the mixing-free transport of a heterogeneous liquid between two locations in a channel system.

TECHNICAL FIELD OF APPLICATION

Heterogeneous liquids, i.e. liquids comprising concentration gradients of molecules or microparticles (e.g. beads), are produced in a variety of synthetic or analytical tasks in the chemical sector. Above all in connection with flow reactors or separation processes, such as chromatography and gel electrophoresis (PAGE) in the field of biotechnology, but also in the field of combinatorial chemistry or in "Lap on a chip" applications, heterogeneous liquids must be transported in a mixing-free manner from the location of their production to the location of further treatment (e.g. analysis, fractioning or other treatment steps).

STATE OF THE ART

In conventional analysis processes, such as chromatography or electrophoresis, heterogeneously fractioned solutions suffer, during their transport within capillary systems, from a strong longitudinal mixing, which strongly reduces their dissolution capacity. This is due to the development of the well-known parabolic velocity profile which causes the flow in the middle of the channel or the capillary to move faster than at the edge. Consequently, a lateral diffusion causes, over short distances, the longitudinal mixing in the flow (G. Taylor Convection, cf. "Dispersion of soluble matter in solvent flowing slowly through a tube, Proc. Roy. Soc., London 219A (1953) 186-203). Although a decrease in the tube diameter reduces the overall mixing, it increases the hydrodynamic resistance and causes larger problems due to wall effects and adsorption. Recent research has shown that a targeted lateral mixing caused by microstructured components reduces this effect to a certain degree (cf. M. J. Clifton "Continuous flow electrophoresis in the Taylor regime", J. Chromatography A 757 (1997) 193-202). However, this so-called "Taylor dispersion" and the wall adsorption remain limiting factors for a continuous single-phase sample transport in capillaries.

Spontaneous phase separations of immiscible liquids are known (cf. K.-V. Schubert and E. W. Kaler "Nonionic microemulsions", Ber. Bunsengesellschaft 100 (1996) 190-205). Thus, for example, equilibrium oil and water form a two-phase system. The production of droplets from immiscible phases within microchannels has also been analysed. In contrast, the utilization of droplets from immiscible phases for the mixing-free transport of microscopic sample volumes has not yet been described. Further, the control of non-equilibrium phase formation through surface, geometry and flow velocity effects has been the subject of little research so far (cf. L. M. Grant and W. A. Ducker "Effect of Substrate Hydrophobicity on Surface-Aggregate Geometry", J. Phys. Chem. B101 (1997) 5337-5345). Surface properties such as hydrophobicity and hydrophilicity are utilized in targeted positioning of droplets at open surfaces and keeping them at defined locations (e.g. in water-air systems). The formation of droplet chains in air-water systems and oil-water systems is known (cf. "Droplet formation in a microchannel network", Takasi Nisiako, Toru Torii, Toshiro Higuchi, Lab on a Chip, Vol. 2, No. 1 (2002) and "Dynamic Pattern Formation in a Vesicle-Generating Microfluidic Device", Todd Thorsen, Richard W. Roberts, Frances H. Arnold and Stephen R. Quake, Physical Review Letters, Vol. 86, No. 18 (2001)), but not their utilization in connection with autonomous separation of droplets for targeted transport of heterogeneous samples. Water-air systems have the further drawback that they are adapted to expand under changing pressure conditions and are not precisely controllable.

OBJECT ACHIEVED BY THE INVENTION

The invention describes a device and a method for "digitally" encoding and decoding heterogeneous liquids in discrete droplets, which is rendered possible by mixing-free transport within capillaries and/or microchannels.

Solution

According to the invention, this objective is achieved with a method for mixing-free transport of a heterogeneous liquid, i.e. a liquid which, as seen in the direction of flow, comprises a inhomogeneous component, in microchannels, wherein in the method a first heterogeneous liquid flows through a first channel and, at a first connecting location, meets a second channel carrying a second liquid (hereinafter referred to as separating liquid, wherein this second liquid may be homogeneous or inhomogeneous), wherein the two liquids are selected such that they can interact so as to cause a phase separation, the two liquids, at the connecting location, are converted into a two-phase flow (hereinafter referred to as droplet chain) of alternating volume fractions of the first and the second liquid by formation of stable or metastable non-equilibrium phases in particular due to surface properties (e.g. structure, deposits, films), geometries and/or flow velocities, and this two-phase flow passes through a transmission channel extending from the first connecting location of the first channel with the second channel, and the two-phase flow, after its transmission and at another connecting location of the transmission channel with a third and a fourth channel, is spontaneously divided, in particular due to surface properties (e.g. structure, deposits, films), geometry and/or flow velocities, into the third and the fourth channels as the liquid flows that existed prior to the separation.

Thus, according to the invention, a heterogeneous liquid flow is divided into portions by introducing individual volume fractions of a second liquid, which may be but need not be homogeneous, between successive volume fractions of the heterogeneous liquid. While these volume fractions of the heterogeneous liquid, lying close to one another, would mix without this measure being taken, separation of the individual volume fractions allows these volume fractions, and thus the heterogeneous liquid, to be transported over large distances without any mixing occurring. Treatment of the volume fraction requires separation of the liquid flow of alternating volume fractions of the two liquids so that again two flows are produced one of which being the heterogeneous starting liquid and the other being the second liquid. Since both processes can take place autonomously by self-organization of the phases, an overall solution for the mixing-free transport of a heterogeneous liquid without employment of expensive fractionating apparatus can be achieved.

The combination of the two liquid flows as well as the separation of the overall flow into the two liquid flows occur at connecting locations at which the respective channels meet each other. At these connecting locations chambers may be formed.

Preferred embodiments of the invention are stated in the subclaims.

Fundamentals of the Solution

The following subitems 1-3 describe an apparatus for mixing-free transport of heterogeneous liquids in capillaries or microchannels with characteristic cross-section/structure sizes (width, depth) between 1 µm and 5 mm rendered possible by an autonomous "inline" formation and separation of alternating droplet chains with the aid of a second liquid which is immiscible with the starting solution.

1. Defined Droplet Formation by Kinetic Self-organization and Self-production

A second liquid, which is immiscible with the first phase and adapted to expand to a small extent, is selected. The two liquids should clearly differ from each other with regard to their contact angle to the channel wall. The heterogeneous components of the first liquid may not be soluble in the second phase (separation liquid). For an aqueous solution of biopolymers for example oils are suitable. The formation of alternating fluid phases (such as oil/lipid and water droplets), with or without additives influencing the surface tension, of two or more fluids, which are immiscible with each other, in a continuous flow is controlled at the meeting point of two or more capillaries (diameter 5-5000 µm) or microchannel structures (structure width 1-5000 µm, structure height 1-5000 µm). The principle of the procedure is shown in the drawing. The droplet formation is a kinetic procedure which results in a non-equilibrium state. The droplet length (mostly larger than the channel diameter) and thus the droplet volumes (fl-µm) depend on the volume of the meeting chamber and/or their meeting and/or crossing point. Further variables influencing the process are: the selection of the second phase (see above), the geometry of the meeting chamber, the wetting properties of the walls/capillary surfaces as well as the selection of various flow rates. The embodiment shows detailed values for two different cases.

2. Autonomous Separation of Alternating Droplet Chains

The autonomous separation of alternating fluid phases (such as oil and water droplets) under flow conditions is controlled by branching capillaries (diameter 5-5000 µm) or microchannel structures (structure width 1-5000 µm, structure height 1-5000 µm). Due to the different wetting properties of the liquids, the aqueous state is discharged in the drain channel with the hydrophilic surface and the oil phase (separation liquid) is discharged in the drain channel with the hydrophobic surface. In addition, the volume of the separation chamber relative to the volume of the droplets should be correspondingly small. The two liquids are then neatly separated in the two discharge channels (or capillaries) while flowing at the same velocity as stated under item 1. Exact conditions for a preferred aspect of the invention are stated in the embodiment.

3. Combination of Items 2 and 1 with Recovery of the Separation Phase Used

A complete transfer apparatus requires employment of a reservoir for the separation-phase liquid (e.g. oil/lipid) and a pump for pumping the liquid from the reservoir. To keep the consumption of the separation-phase liquid at a low level, the second phase can be recovered. The separation phase is returned, with the aid of the pump system, to the location where the formation process takes place (item 1) such that the systems constitutes a closed circuit.

Improvements and Advantages as Compared with the State of the Art

The transport of heterogeneous molecule samples (in particular in the aqueous phase) split into droplets can take place without the molecules mixing with each other (prevented by the separation phase, e.g. oil droplets), provided that the molecules are not soluble in the second phase. By utilization of mobile droplets heterogeneous samples can thus be separated and transported over larger distances (e.g. several meters) without any mixing occurring. In this manner, such separated samples can be transported to the location of a following synthesis step or another analysis. In suspensions of micro-/nanoparticles, too, droplets containing defined quantities of particles (beads) can be formed and fed to the desired reaction and/or analysis locations. Advantage: improvement of the reproducibility of analyses/diagnostic procedures.

BRIEF DESCRIPTION OF THE DRAWINGS

FIG. 1 shows an embodiment of the invention.

DESCRIPTION OF THE PREFERRED EMBODIMENTS

Hereunder the invention is explained in detail with reference to an embodiment shown in the drawing.

Two liquids in the corresponding inlet channels/capillaries meet in a meeting chamber 10 and autonomously form a droplet chain 12. In the example, a heterogeneous aqueous liquid 14 and an oil/lipid phase 16 are shown as liquids that are immiscible with each other. However, other immiscible phases can also be used.

The heterogeneous aqueous liquid 14 is, for example, constituted by individual sample volumes lying one behind the other which are produced in a sample treatment unit 18 and arranged in series as seen in the direction of flow. This heterogeneous solution is now to be transported to a location at a relatively large distance from the production site, where the solution is subjected to further treatment (for example, analysed, fractioned or subjected to other treatment steps). This location is generally shown in the drawing as treatment location 20. The problems encountered are that the individual sample volumes can mix with each other when the heterogeneous aqueous solution is transported over a larger distance, whereas the transport over a relatively short distance (for example, up to 1 cm) does not lead to any disturbing mixing. Therefore, the heterogeneous aqueous liquid is transported from the unit 18 via a short channel 22 to the meeting chamber 10. In this meeting chamber 10 the oil/lipid phase 16 is added via a channel 24.

In the meeting chamber 10, due to the mechanisms described above (cf. the aforementioned citations), a spontaneous phase separation of the two flows occurs and the droplet chain 12 is formed in a channel 26 extending from the meeting chamber 10. This droplet chain 12 comprises volume fractions alternately lying one behind the other of the heterogeneous aqueous solution 14 and the oil/lipid phase 16. The separation takes place in the meeting chamber 10 such that the individual sample volumes of the aqueous solution 14 are now separated from each other by the oil/lipid volumes. Thus the sample volumes do not mix with each other in the channel 26.

For further treatment of the sample volumes in the unit 20, the individual sample volumes must be recombined to again form a heterogeneous aqueous solution flow. For this purpose, the droplet chain 12 is separated in a separation chamber 28 into which the channel 26 leads. The heterogeneous aqueous solution 14, comprised of the successive individual sample volumes, flows out via a first outlet channel 30, while the oil/lipid phase 16 flows out via a second outlet channel 32. This second outlet channel 32 can be connected via a pump 34 with the first channel 24 to form a circulation system for the oil/lipid phase. In this circulation system, a reservoir 36 can be arranged. The pump 34 is required on the one hand to allow substance circulation, and on the other hand to control the transport velocity.

Droplet Formation (in the Meeting Chamber 10)

The formation of very small droplets is achieved by the combination of low flowing velocities (with magnitude of <1 µl/min.) and small volumes at the crossing point (in the magnitude of some nl). At higher flow rates (in the magnitude of >0.05 ml/min.) a "nozzle effect" is utilized which occurs when oil/lipid is introduced into the flow of an aqueous phase.

(i) Low Flow Rates:

In a T-section (wall material untreated silicon; channel width 300 µm; channel depth 50 µm, volume of the meeting chamber 5 nl) water and oil are combined as shown in the drawing. If the meeting volume is filled with one of the two liquids and then identical flow rates of the two liquids are set, water and oil alternately flow into the meeting volume, provided that the flow rates do not exceed 1 µm/min. In the discharge channel by this means chains of alternating droplets of the two liquids with a droplet volume of 100 nl can be observed. If the volume of the droplets formed is scaled to the volume of the meeting chamber, the channel width of a T-section (channel depth again 50 µm), in which the droplets of a volume of 500 pl are formed, can be reduced to approximately 5 µm.

(ii) High Flow Rates:

Polyethylene tubes (inner diameter 400 µm) are connected via a silicone adapter tube (hydrophobic, inner diameter 500 µm) to a Y-section (hydrophilic wall material, e.g. glass; line diameter 200 µm; length of line as from crossing point 8 mm). Via two of the tubes water and oil are transported into the Y-section. At a constant flow rate of the water of 0.05 ml/min., oil flows at flow rates of more than 0.2 ml/min. through the meeting chamber without contacting the hydrophilic glass walls of the Y-section. The water flows between the oil and the glass wall into the discharge line. Formation of the droplets takes place at the transition between the glass Y-section and the silicone tube due to a "nozzle effect" and is promoted by the change in the wetting properties of the walls. The water droplets have a volume of 90 nl, the oil droplets have a volume of 300 µm at a flow rate of 0.2 ml/min.

Separation (in the Separation Chamber 28)

Into a T-section (one of the arms having hydrophilic, the opposite arm having hydrophobic walls; channel width 10 µm, channel depth 50 µm; volume of the meeting chamber 5 pl) a chain of alternating droplets of water and oil (droplet volume 1 nl) is transported at flow rates not exceeding 0.1 µm/min. The chain of alternating droplets is separated into an oil flow and a water flow which flow out through the hydrophobic line and the hydrophilic line, respectively.

Transport System

The two system components (droplet formation/separation) can be combined, as shown in the drawing, for the purpose of transporting heterogeneous liquids in a closed-circuit system. In many analysis processes (e.g. chromatography) samples are separated and heterogeneous solutions are produced such as are also produced during kinetic processes in flow reactors. The existing concentration gradients at the output of the measuring instrument and/or the reactor can be separated into small microsample volumes with the aid of the described process for droplet formation and then transported in a mixing-free manner over long distances to locations of further treatment. There or after the treatment step, the droplet chains can be recombined and/or separated into their phases.

The invention claimed is:

1. Method for mixing-free transport of a heterogeneous liquid in microchannels, wherein in the method a first heterogeneous liquid (14) flows through a first channel (22) and, at a first connecting location (meeting chamber 10), meets a second (24) channel carrying a second liquid (16), wherein the two liquids (14,16) are selected such that they cooperate to cause a phase separation, the first and second liquids (14,16), at the connecting location (meeting chamber 10), are converted into a two-phase flow (droplet chain 12) of alternating volume fractions of the first and second liquids (14,16) by formation of non-equilibrium phases in particular due to surface structures, deposits or films, geometries and/or flow velocities, and this two-phase flow (droplet chain 12) passes through a transmission channel (26) extending from the connecting location (meeting chamber 10) of the first channel (14) with the second channel (24), and the two-phase flow (droplet chain 12), after this transmission and at another connecting location (separation chamber 28) of the transmission channel (26) with a third and a fourth channel (30,32), is spontaneously divided, in particular due to surface structures, deposits or films, geometry and/or flow velocities, into the third and fourth channels (30,32) as the liquid flows that existed prior to the separation.

2. Method according to claim 1, characterized in that at least one of the heterogeneous liquids comprises microparticles, such as beads.

3. The method of claim 2, wherein the method is applied in chromatography, in particular for protein purification or other (chemical) separation processes.

4. The method of claim 2, wherein the method is applied for transporting heterogeneous microparticles, in particular beads, distributed in at least one of the liquids.

5. The method of claim 1, wherein the method is applied in chromatography, in particular for protein purification or other (chemical) separation processes.

6. The method of claim 1, wherein the method is applied for transporting heterogeneous microparticles, in particular beads, distributed in at least one of the liquids.

* * * * *